United States Patent [19]
Jackson et al.

[11] Patent Number: 5,997,478
[45] Date of Patent: Dec. 7, 1999

[54] ULTRASOUND SYSTEM AND METHOD FOR FACILITATING A REPRODUCIBLE ULTRASOUND IMAGING ENVIRONMENT

[75] Inventors: John I. Jackson, Menlo Park; James W. Arenson, Woodside, both of Calif.

[73] Assignee: Acuson Corporation, Mountain View, Calif.

[21] Appl. No.: 09/017,756

[22] Filed: Feb. 3, 1998

[51] Int. Cl.$^6$ ...................................................... A61B 8/00
[52] U.S. Cl. ............................................................ 600/437
[58] Field of Search ........................... 600/437, 441–443, 600/447, 458

[56] References Cited

U.S. PATENT DOCUMENTS

5,636,631  6/1997  Waiz et al. ............................... 600/437
5,851,186  12/1998 Wood et al. .............................. 600/437
5,853,367  12/1998 Chalek et al. ........................... 600/437

*Primary Examiner*—Francis J. Jaworski
*Attorney, Agent, or Firm*—Brinks Hofer Gilson & Lione

[57] ABSTRACT

An ultrasound system and method are presented for facilitating a reproducible ultrasound imaging environment by reducing the variability in ultrasound parameters as a source of discrepancy when performing serial studies. In this way, an operator can rigorously compare ultrasound images from a single patient and can ensure that a plurality of patients are imaged in the same way. Additionally, an imaging environment can be duplicated on a plurality of ultrasound systems. This is especially helpful in ensuring that several machines are configured in the same way and in tracking down unexpected behavior (e.g., hardware or software bugs or anomalies).

46 Claims, 5 Drawing Sheets

ULTRASOUND SYSTEM AND METHOD FOR FACILITATING A REPRODUCIBLE ULTRASOUND IMAGING ENVIRONMENT

BACKGROUND

Ultrasound images provide an operator with a wide range of information about a patient. To gain more information, it often is necessary to reproduce the ultrasound imaging environment that existed when an ultrasound image was created. For example, when an operator compares ultrasound images of a patient over time or performs serial studies on a plurality of patients, it is necessary to ensure that patients are imaged in the same way to remove ultrasound imaging system setup variability as a source of discrepancy. Reproduction of an ultrasound imaging environment is made extremely difficult or impossible due to the variations in, for example, the ultrasound system, the transducer, environmental noise, thermal and electrical noise, transducer placement, patient physiological change, operator placement of the transducer on the body, and the amount of acoustic coupling between the transducer and the body.

Another source of difficulty in reproducing an ultrasound imaging environment is due to the large number of operator-controlled parameters that adjust the transmission of the ultrasound beam(s) and the processing, scan conversion, and display of received ultrasound data. Several imaging modes and sub-modes typically are available to an operator. For each of these modes and sub-modes, the operator has a wide range of imaging controls at his or her disposal. These imaging controls include the number of transmit focal beams, the transmit beam focal depths, the transmit power amplitude, the minimum and maximum depth over which the ultrasound image is displayed, the overall receiver gain and localized gain, imaging frequency, spatial filtering, temporal filtering, dynamic range or log compression, postprocessing, Doppler filters, Doppler gate size, the angle of the first and last ultrasound lines, the density of the ultrasound lines, and the size and orientation of the displayed image.

One attempt to reproduce an ultrasound imaging environment is to use pre-stored parameter-setting packages based on an intended clinical application (e.g., obstetrics, peripheral vascular, cardiology). By using the same parameter package, an operator can reduce the variability in ultrasound parameters. The difficulty with this approach is that the operator typically refines the recalled parameters to best visualize the structures of interest on each patient. For example, parameters such as the receiver gain and frequency typically change throughout the course of a clinical ultrasound exam. Thus, even if the operator uses the same parameter package in another imaging session, the imaging environment would not be the same. Accordingly, parameter-setting packages are insufficient for conducting precise, controlled serial studies on a set of patients or for reproducing the imaging parameters that were used to acquire a specific image on a specific patient at some previous point in time.

Another attempt to reproduce an ultrasound imaging environment is to label stored ultrasound images with some of the parameters that were used to create the image. By recalling a stored image, an operator can read the parameters from the stored image and manually adjust the parameters of the imaging system to be identical or similar to those used to acquire the stored image. Several system parameters, however, are difficult or impossible to store in this format. Without storage and retrieval of such parameters, a substantially identical ultrasound imaging environment can not be reproduced.

There is, therefore, a need for an improved ultrasound system and method for facilitating a reproducible ultrasound imaging environment.

SUMMARY

The present invention is defined by the following claims, and nothing in this section should be taken as a limitation on those claims.

By way of introduction, the preferred embodiments described below include an ultrasound imaging system and method that can be used to facilitate a reproducible ultrasound imaging environment by reducing the variability in ultrasound parameters. With such a system and method, an operator can rigorously compare ultrasound images from a single patient and can ensure that a plurality of patients are imaged in the same way. A further benefit to these embodiments is that they provide a convenient way of duplicating an imaging environment on a plurality of ultrasound systems. This is especially helpful in ensuring that several machines are configured in the same way and in tracking down unexpected behavior (e.g., hardware or software bugs or anomalies).

The preferred embodiments will now be described with reference to the attached drawings.

DETAILED DESCRIPTION OF THE PRESENTLY PREFERRED EMBODIMENTS

Figure 1:
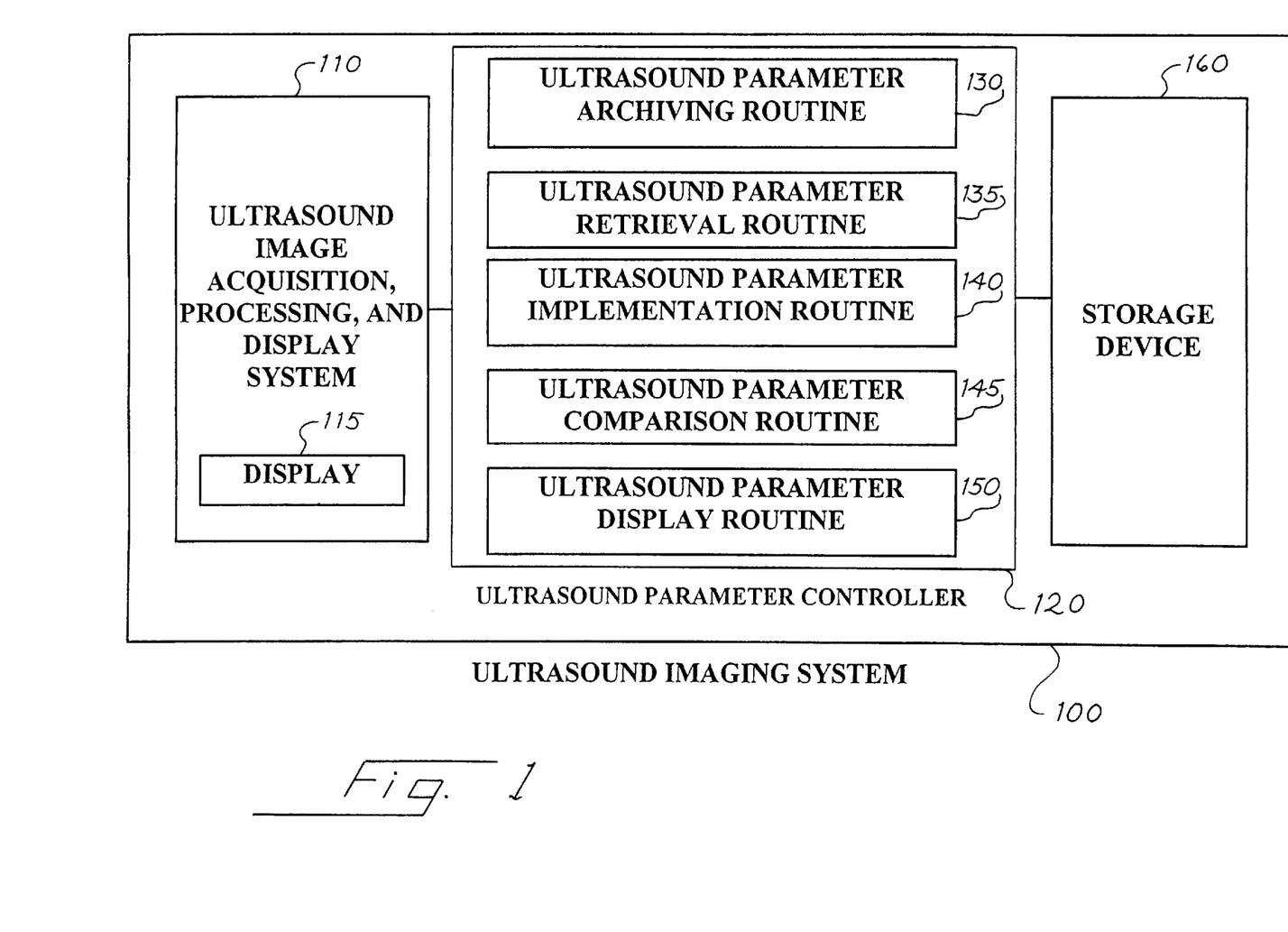
FIG. 1 is a block diagram of an ultrasound imaging system of a preferred embodiment.
Figure 2:
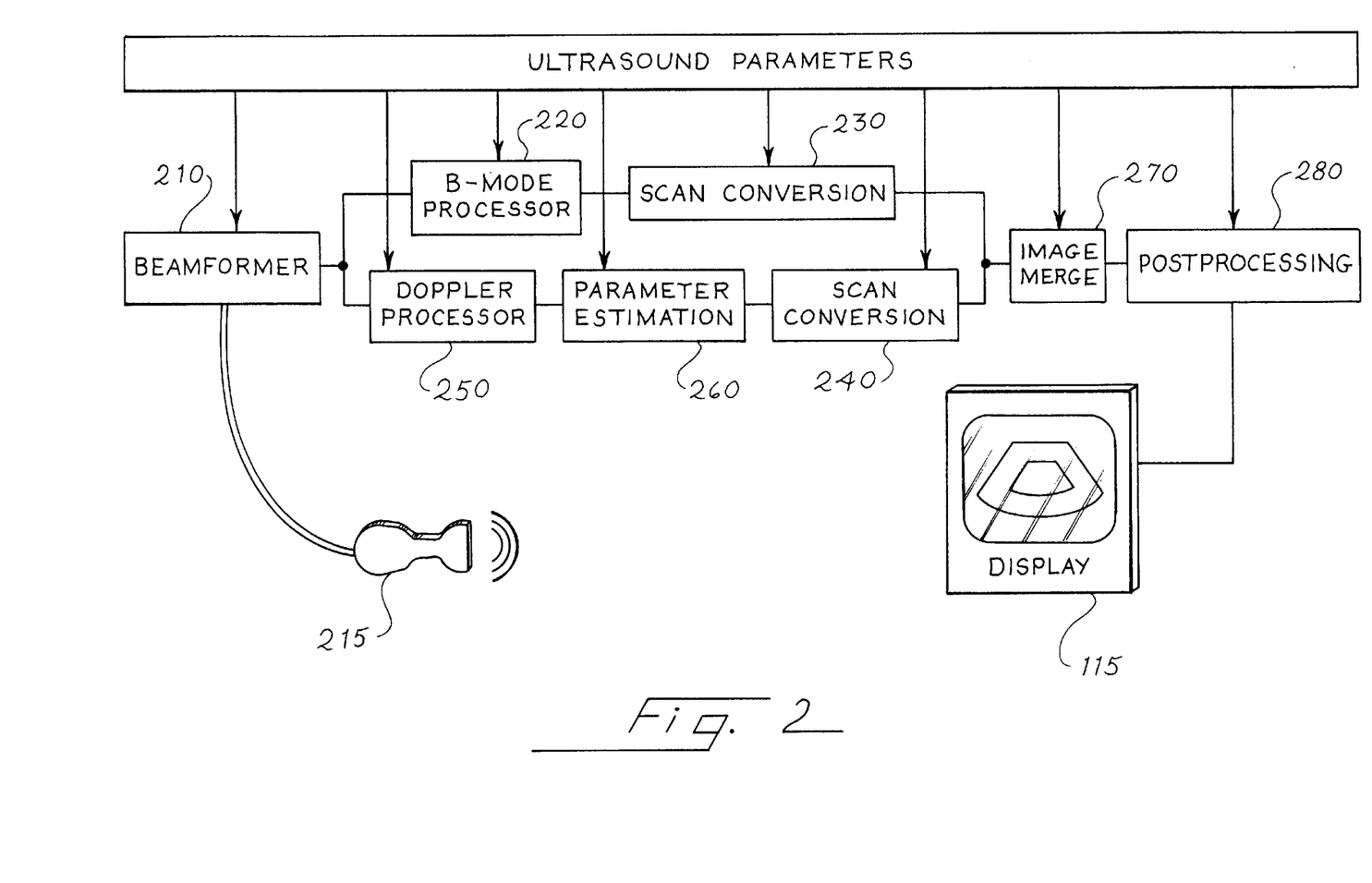
FIG. 2 is a block diagram of an ultrasound image acquisition, processing, and display system of a preferred embodiment.

Turning now to the drawings, FIG. 1 shows a block diagram of an ultrasound imaging system 100 of a preferred embodiment. This system 100 comprises an ultrasound image acquisition, processing, and display system 110, which includes a display 115. As shown in FIG. 2, the ultrasound image acquisition, processing, and display system 110 can comprise a beamformer 210, which is coupled with a transducer 215, a B-mode processor 220, first 230 and second 240 scan conversion units, a Doppler processor 250, a parameter estimation unit 260, an image merger 270, a postprocessing unit 280, and a display 115. As used herein, the term "coupled with" means directly coupled with or indirectly coupled with through one or more components. It is important to note that the components shown in FIG. 2 are presented merely for illustration and that other components may be used.

Turning again to FIG. 1, the ultrasound image acquisition, processing, and display system 110 is coupled with an ultrasound parameter controller 120 and a storage device 160. The ultrasound parameter controller 120 comprises an ultrasound parameter archiving routine 130, an ultrasound parameter retrieval routine 135, an ultrasound parameter implementation routine 140, an ultrasound parameter comparison routine 145, and an ultrasound parameter display routine 150. While it is preferred that these routines be implemented with software and that the ultrasound parameter controller 120 comprise the necessary hardware components (such as a CPU) to run the software, it is important to note that any appropriate hardware, analog or digital, and any appropriate software language can be used. It also is important to note that although these routines are shown as distinct elements in FIG. 1, the routines can be combined. Further, while the ultrasound parameter controller 120 is shown separate from the ultrasound image acquisition, processing, and display system 110, the controller 120 can be part of the system 110. For example, the ultrasound parameter controller 120 can be part of a general controller used to direct the operation of the ultrasound image acquisition, processing, and display system 110.

With these components, the ultrasound imaging system 100 of FIG. 1 can implement several methods to reduce ultrasound parameter variability to facilitate a reproducible ultrasound imaging environment. As described below, these methods include a method for automatically comparing ultrasound parameters, a method for automatically implementing a retrieved user-adjusted ultrasound parameter, and a method for automatically displaying a retrieved ultrasound parameter.

Figure 3:
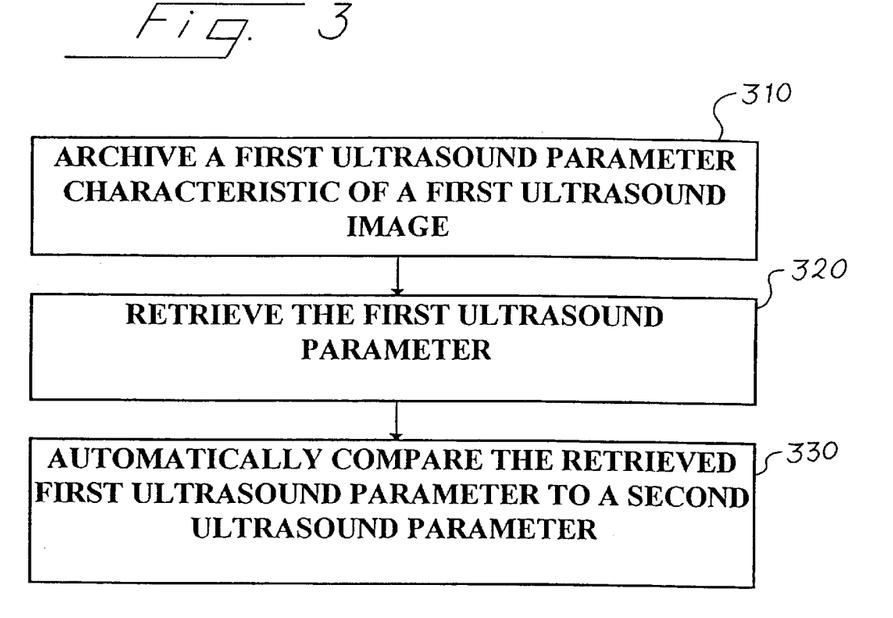
FIG. 3 is a flow chart of a method of a preferred embodiment for automatically comparing ultrasound parameters.

The system 100 of FIG. 1 can be used in a method for automatically comparing ultrasound parameters. As shown in FIG. 3, this method comprises the steps of archiving a first ultrasound parameter characteristic of a first ultrasound image (step 310), retrieving the first ultrasound parameter (step 320), and automatically comparing the retrieved first ultrasound parameter to a second ultrasound parameter (step 330). The first step in this method is to archive a first ultrasound parameter characteristic of a first ultrasound image (step 310). An operator can select which ultrasound parameters will be archived and direct the ultrasound parameter archiving routine 130 to archive the parameters at a particular time. Alternatively, the ultrasound parameter archiving routine 130 can select and/or archive the parameters automatically. The actual parameter setting or an index value can be archived for some or all of the ultrasound parameters. Instead of archiving only the ultrasound parameters, the ultrasound parameter archiving routine 130 can archive an ultrasound image along with the parameters. Depending on the intended application (e.g., repeat exams on a specific patient or a series of exams across different patients), the parameters can be archived by themselves with an identifying name/label and/or time stamp, or they can be archived as an attachment to a digital image or a set of images (e.g., a digital video clip). In one embodiment, the operator can select, via a keyboard control, for example, whether or not the ultrasound parameters are archived with a specific image.

The next step is to retrieve the first ultrasound parameter (step 320). The ultrasound parameter retrieval routine 135 recalls the archived parameters from the storage device 160 and loads them into random access memory of the ultrasound parameter controller 120 or the ultrasound image acquisition, processing, and display system 110. If a parameter is archived along with an archived image, the operator can prompt the ultrasound parameter retrieval routine 135 to retrieve the image along with the parameter, or, alternatively, the ultrasound parameter retrieval routine 135 can automatically retrieve the image with the parameter. As described below, the recalled parameters can be from a previous study of a current patient or of another patient to facilitate comparative studies across a population of patients.

The third step in this method is to automatically compare the retrieved first ultrasound parameter to a second ultrasound parameter (step 330). For each parameter to be compared, the ultrasound parameter comparison routine 145 compares the recalled parameter value with a current "in-use" parameter, which is acquired from a memory unit of the ultrasound image acquisition, processing, and display system 110 or the ultrasound parameter controller 120. Equal parameter values can be ignored, and any discrepancies in parameters can be noted on the display 115 with a message noting a description of the parameter (e.g., system software version), the recalled parameter (e.g., 1.00), and the currently active value (e.g., 1.02). As described below, the recalled parameter also can be automatically implemented.

The advantage of comparing ultrasound parameters is that through the display of anomalies or differences in ultrasound parameters, the operator can know which components to adjust and what adjustments to make. If the same imaging system is used to acquire multiple ultrasound images, comparing parameters to decide whether changes in system performance are appropriate will help an operator track down unexpected behavior (e.g., hardware or software bugs or anomalies) that may appear on an ultrasound machine. If different imaging systems are used, comparing parameters ensures that the systems will be configured in the same way.

Figure 4:
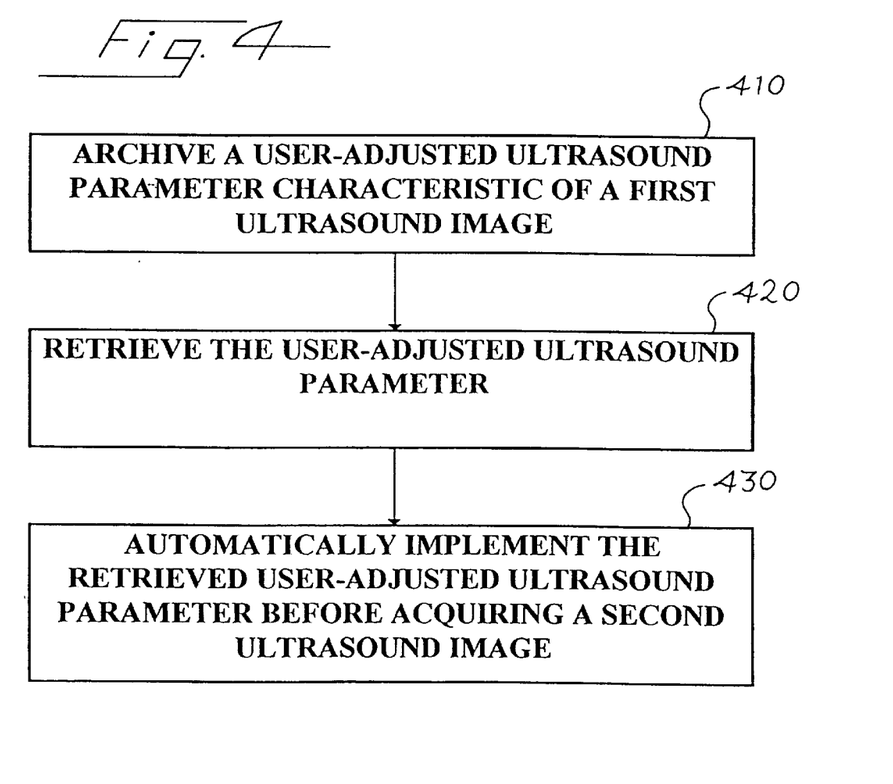
FIG. 4 is a flow chart of a method of a preferred embodiment for automatically implementing a retrieved user-adjusted ultrasound parameter.

The system 100 of FIG. 1 also can be used in a method for automatically implementing a retrieved user-adjusted ultrasound parameter, as shown in FIG. 4. This method comprises the steps of archiving a user-adjusted ultrasound parameter characteristic of a first ultrasound image (step 410), retrieving the user-adjusted ultrasound parameter (step 420), and automatically implementing the retrieved user-adjusted ultrasound parameter before acquiring a second ultrasound image (step 430). The steps of archiving (step 410) and retrieving (step 420) are as described above in reference to FIG. 3. After the parameters are recalled, the ultrasound parameter implementation routine 140 automatically implements the retrieved parameters (step 430). The ultrasound parameter implementation routine 140 automatically configures the appropriate components of the ultrasound image acquisition, processing, and display system 110 by passing the retrieved parameter to the appropriate software controller for implementation. For example, if the parameter is the number of transmit focal beams, the ultrasound parameter implementation routine 140 configures the beamformer to transmit the recalled value of transmit focal beams. In this way, the system operates as if the user had manually specified the parameter through a user-interface. When more than one parameter is archived and retrieved, the parameters can be implemented as a set. For example, the parameters for field of view for color Doppler (which comprises parameters for the first line, the last line, the starting depth, and the ending depth) can be implemented together as a set.

Unlike pre-stored parameter-setting packages, the method of this preferred embodiment recalls the parameters that the user adjusted to create an ultrasound image. The difficulty with parameter-setting packages is that the operator refines the recalled parameters to best visualize the structures of interest on each patient. Thus, even if the operator uses the same parameter-setting package in another imaging session, the imaging environment would not be the same. By archiving and recalling the exact parameters that were used, a more accurate reproduction of the ultrasound imaging environment can be obtained. With such an environment, precise, controlled serial studies can be performed on a set of patients or on a single patient over a period of time.

If the parameters are recalled to a different ultrasound imaging system than the one from which the parameters were archived, the different ultrasound imaging system may not be able to implement the recalled parameters. For example, parameters that are stored from a fully-featured ultrasound system may contain parameters that are not applicable or available on a different product configuration of the same system type. In that case, the operator can be alerted (e.g., via a displayed message) that the retrieved parameter cannot be implemented.

Figure 5:
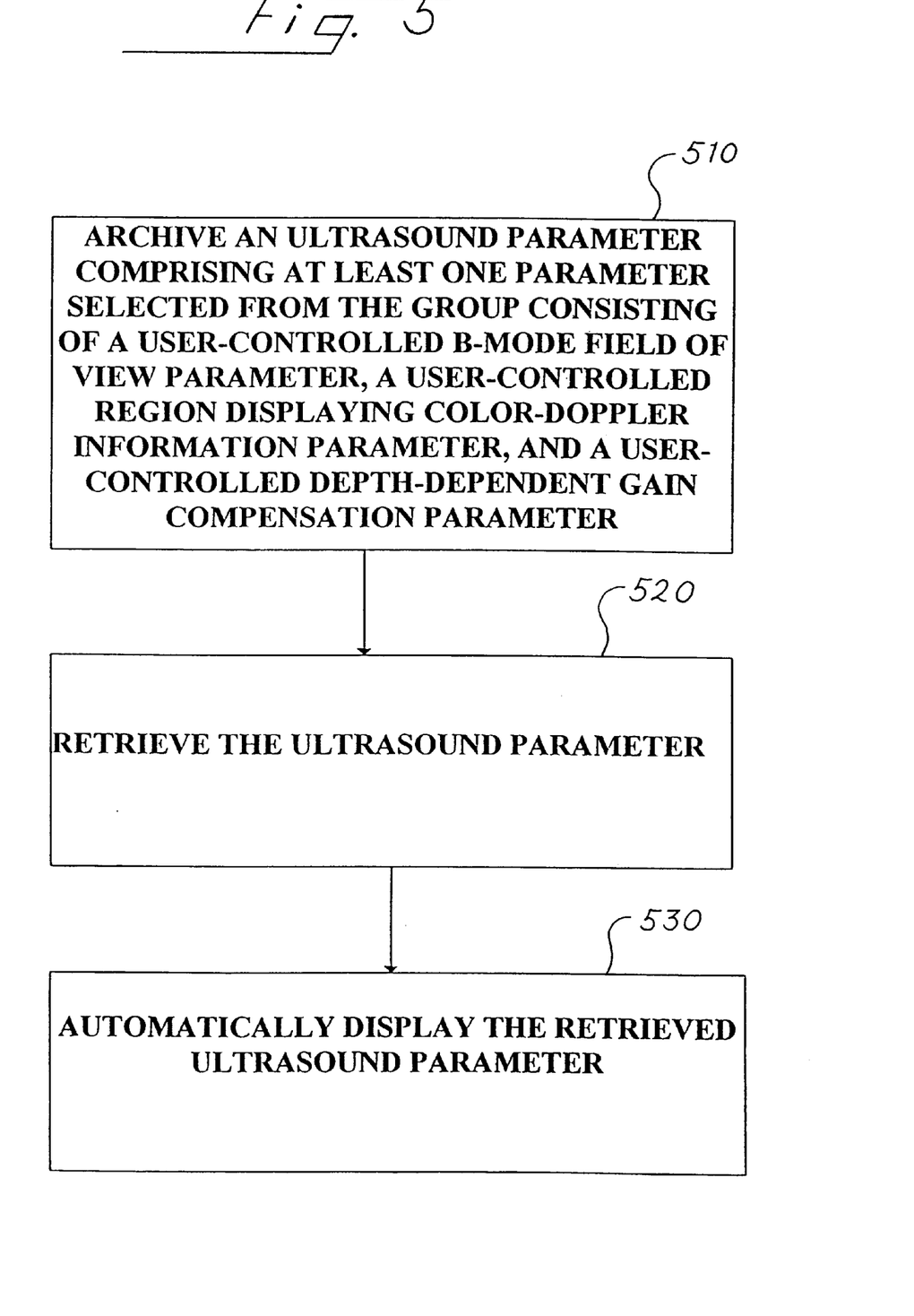
FIG. 5 is a flow chart of a method of a preferred embodiment for automatically displaying a retrieved ultrasound parameter.

Another method that can be implemented with the system 100 of FIG. 1 is a method for automatically displaying a retrieved ultrasound parameter. As shown in FIG. 5, this method comprises the steps of archiving an ultrasound parameter comprising at least one parameter selected from the group consisting of a user-controlled B-mode field of view parameter, a user-controlled region displaying color-Doppler information parameter, and a user-controlled depth-dependent gain compensation parameter (step 510), retrieving the ultrasound parameter (step 520), and automatically displaying the retrieved ultrasound parameter (step 530). The steps of archiving (step 510) and retrieving (step 520) are as described above in reference to FIG. 3. After the parameters are recalled, the ultrasound parameter display routine 150 presents the recalled parameters on the display 115 (step 530). Using a user interface, for example, the operator then can manually configure components of the ultrasound image acquisition, processing, and display system 110 to create the same imaging environment that existed when the ultrasound parameters were archived.

As described above, conventional systems that label stored ultrasound images with parameters do not label images with several parameters that are needed to reproduce an ultrasound imaging environment. This method archives these parameters, which include a user-controlled B-mode field of view parameter, a user-controlled region displaying color-Doppler information parameter, and a user-controlled depth-dependent gain compensation parameter. By recalling an archived image labeled with these parameters, an operator can read the parameters and manually adjust the imaging system's components to reproduce the ultrasound imaging environment.

Figure 6:
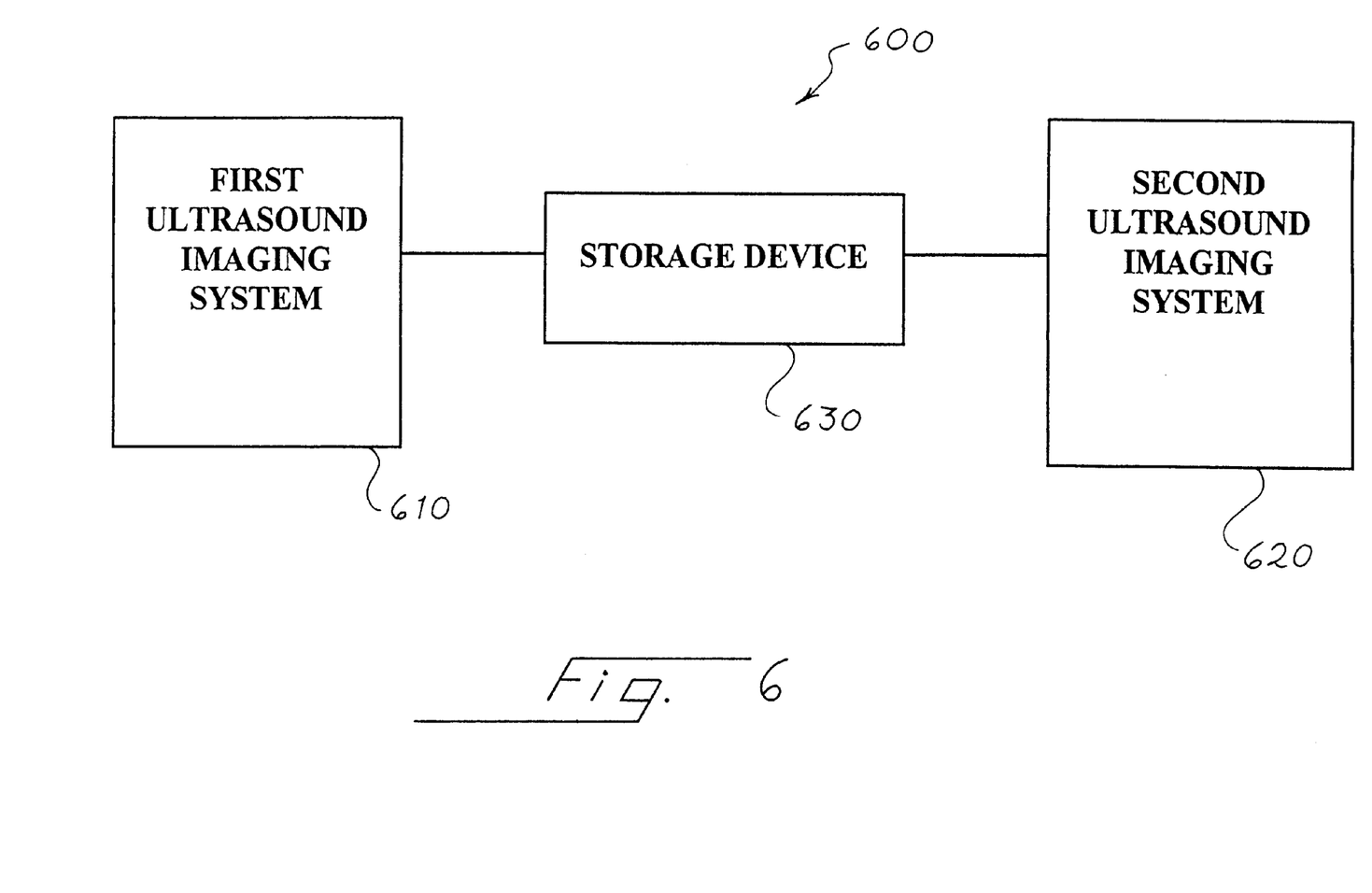
FIG. 6 is a block diagram of a diagnostic medical imaging network of a preferred embodiment.

The above-described embodiments should not be read to limit the invention in any way and are meant to illustrate a few of the many forms the invention can take. For example, while the storage device 160 is shown as part of the imaging system 100 in FIG. 1, the storage device 160 also can be located within a diagnostic medical imaging network, if the imaging system is connected into such a network 600, as shown in FIG. 6. As shown in FIG. 6, a first ultrasound imaging system 610 and a second ultrasound imaging system 620 are coupled with a remotely located storage device 630. It is important to note that some or all of the routines described above can be located in an ultrasound imaging system or in a controller remote from an ultrasound imaging system in the diagnostic network 600. It also is important to note that while two ultrasound imaging systems are shown in FIG. 6, the embodiments described above can be adapted for use with one ultrasound imaging system and a remotely located storage device.

In any of the above embodiments, the storage device 160 can be, for example, a permanent hard drive or a transportable medium, although other types of storage devices can be used. The ultrasound parameters can be stored in a portable data device, a hard-wired network, or in an ultrasound system, preferably in a battery-backed memory or other medium where the parameters will not be lost when the system is powered down.

In one preferred embodiment, the ultrasound imaging system is configured to both automatically compare system identification parameters and implement the user-adjustable parameters. Preferably, the parameters that are archived for later recall include software versions for all software modules; hardware versions for each hardware system or board; all user-controllable options relating to (a) the transmission and reception of ultrasound, (b) the processing of returned ultrasound signals, and (c) the quantification of those signals; parameters relating to the conversion of the returned ultrasound signals to an image; parameters relating to the display of the image; and any quantification based on the video image. In another preferred embodiment, these parameters are automatically archived whenever quantification capabilities are in use.

For simplicity, the term "ultrasound parameter" in this specification and the following claims is intended broadly to encompass both ultrasound system identification parameters and user-adjusted ultrasound parameters. These parameters control the acquisition, processing, display, and quantification of an ultrasound image, and, unlike settings that are typically stored, can include a user-controlled B-mode field of view parameter, a user-controlled region displaying color-Doppler information parameter, and a user-controlled depth-dependent gain compensation parameter. These parameters are commonly known as a RES™ enhanced resolution imaging box or ZOOM region location, a Color Pan box location, and a DGC or TGC position, respectively.

The term "ultrasound system identification parameter" is intended broadly to encompass information about components (including any attached peripherals, such as an ultrasonic transducer) that do not regularly change or over which an operator typically has no control. Ultrasound system identification parameters can include, but are not limited to, the serial number of the ultrasound system, the serial number of each hardware board or component within the system, the transducer type and serial number, the model number and serial number of any attached peripheral (such as a video cassette recorder or a page printer), the software version number of the overall system software, the software and/or firmware version number for any sub-system component, the specific software configuration (i.e., the features or components of the software that have been enabled), and the version number of the data file that contains the imaging specification data for a particular ultrasound transducer.

For simplicity, the term "user-adjusted ultrasound parameter" in this specification and the following claims is intended broadly to encompass both ultrasound quantification parameters and ultrasound imaging parameters. The term "ultrasound quantification parameter" is intended broadly to encompass parameters needed to reproduce a quantification or measurement of a displayed image. These parameters include, but are not limited to, the shape, size, and location of quantification regions and the type of quantification being applied to those regions (e.g., the average value of the enclosed pixels, the number of enclosed pixels, a histogram of the enclosed pixels, the area of color Doppler pixels, the average B-mode signal intensity, mean signal energy, and/or mean velocity). Quantification methods are more fully described in U.S. patent application Ser. Nos. 08/753,999 and Ser. No. 08/916,590 which are hereby incorporated by reference and are assigned to the assignee of the present invention.

The term "ultrasound imaging parameter" is intended broadly to encompass information related to the imaging modes of the ultrasound system and to the setting of each operator-controllable parameter relating to each mode. For example, in B-mode imaging (two-dimensional or M-mode, for example), an "ultrasound imaging parameter" can include transmit frequency, receive frequency, transmit power, transmit focus locations, display depth, image size on the display screen, image orientation on the display (left-right inverted, up-down inverted), gain settings (master gain, localized depth and/or lateral gain compensation), azimuthal spacing of ultrasound lines, log compression, spatial filters, temporal filters, and postprocessing curve. If less than the full standard azimuthal range and depth of the image is used, such as in a RES™ or ZOOM mode, additional parameters can comprise the positions of the starting and ending ultrasound lines and the starting and ending depth over which the image is displayed. An "ultrasound imaging parameter" also can include a timing parameter (i.e., the time between acquired images). Timing parameters can include internal signals (such as time), external signals (such as an R-wave of an electrocardiogram or an injection of contrast agent), or any combination thereof.

In color Doppler mode (two-dimensional or M-mode, for example), an "ultrasound imaging parameter" can include class (i.e., whether the display relates to the velocity, variance, energy, or any combination thereof, of a signal returned by blood, or the velocity, energy, acceleration, or any combination thereof, of a signal returned by tissue), transmit frequency, transmit power, transmit focus locations, the positions and/or steering angle of the starting and ending ultrasound lines, the starting and ending depth over which color Doppler information is displayed, log compression, wall filter, spatial filter, temporal filter, gate size, sample repetition interval, receive gain, display threshold level, and postprocessing parameters.

With a pulsed-wave (PW) spectral Doppler mode, an "ultrasound imaging parameter" can include transmit frequency, transmit power, gate depth, gate size, sample repetition interval, steering angle, filter, display size and position, sweep speed, and postprocessing. With continuous-wave (CW) spectral Doppler, an "ultrasound imaging parameter" can include transmit frequency, transmit power, focusing depth, sample repetition interval, steering angle, filter, display size and position, sweep speed, and postprocessing. It is important to note that ultrasound imaging parameters can include parameters in addition to the ones listed above.

The foregoing detailed description has described only a few of the many forms that this invention can take. Of course, many changes and modifications are possible to the preferred embodiments described above. For this reason it is intended that this detailed description be regarded as an illustration and not as a limitation of the invention. It is only the following claims, including all equivalents, that are intended to define the scope of this invention.

What is claimed is:

1. A method for automatically comparing ultrasound parameters, said method comprising the steps of:
   (a) archiving a first ultrasound parameter characteristic of a first ultrasound image; then
   (b) with an ultrasound imaging system retrieving said first ultrasound parameter, and then
   (c) with the ultrasound imaging ststem, automatically comparing said retrieved first ultrasound parameter to a second ultrasound parameter.

2. The method of claim 1, further comprising the step of:
   (d) with the ultrasound imaging system, automatically notifying an operator of a discrepancy between said retrieved first ultrasound parameter and said second ultrasound parameter.

3. The method of claim 1, further comprising the step of:
   (d) with the ultrasound imaging system, automatically implementing said retrieved first ultrasound parameter.

4. The method of claim 1, wherein said first and second ultrasound parameters comprise a system identification parameter.

5. The method of claim 1, wherein said first and second ultrasound parameters comprise a user-adjusted parameter.

6. The method of claim 1, wherein said first and second ultrasound parameters comprise an ultrasound imaging parameter.

7. The method of claim 1, wherein said first and second ultrasound parameters comprise an ultrasound quantification parameter.

8. The method of claim 1, wherein said first and second ultrasound parameters comprise a parameter selected from the group consisting of a user-controlled B-mode field of view parameter, a user-controlled region displaying color-Doppler information parameter, and a user-controlled depth-dependent gain compensation parameter.

9. The method of claim 1, further comprising the step of archiving an ultrasound image with said first ultrasound parameter.

10. The method of claim 9, further comprising the step of retrieving said ultrasound image with said first ultrasound parameter.

11. The method of claim 1, wherein step (a) comprises the step of archiving a first ultrasound parameter characteristic of a first ultrasound image in a storage location in the ultrasound imagine system.

12. The method of claim 1, wherein step (a) comprises the step of archiving a first ultrasound parameter characteristic of a first ultrasound image in a storage location remote from the ultrasound imaging system in a diagnostic medical imaging network.

13. The method of claim 1, wherein (a) comprises archiving a first ultrasound parameter characteristic of a first ultrasound image with an ultrasound imaging system different from the ultrasound imaging system that automatically compares in (c).

14. The invention of claim 1, wherein said first ultrasound parameter is associated with a first patient and wherein said second ultrasound parameter is associated with a second patient.

15. A method for automatically implementing a retrieved user-adjusted ultrasound parameter, said method comprising the steps of:
   (a) archiving a user-adjusted ultrasound parameter characteristic of a first ultrasound image; then
   (b) with an ultrasound imaging system, retrieving said user-adjusted ultrasound parameter; and then
   (c) with the ultrasound imaging system, automatically implementing said retrieved user-adjusted ultrasound parameter before acquiring a second ultrasound image.

16. The method of claim 15, wherein said user-adjusted ultrasound parameter comprises an ultrasound imaging parameter.

17. The method of claim 15, wherein said user-adjusted ultrasound parameter comprises an ultrasound quantification parameter.

18. The method of claim 15, wherein said user-adjusted ultrasound parameter comprises at least one parameter selected from the group consisting of a user-controlled B-mode field of view parameter, a user-controlled region displaying color-Doppler information parameter, and a user-controlled depth-dependent gain compensation parameter.

19. The method of claim 15, further comprising the step of archiving an ultrasound image with said user-adjusted ultrasound parameter.

20. The method of claim 15, wherein step (a) comprises the step of archiving a user-adjusted ultrasound parameter characteristic of a first ultrasound image in a storage location in the ultrasound imaging system.

21. The method of claim 15, wherein step (a) comprises the step of archiving a user-adjusted ultrasound parameter characteristic of a first ultrasound image in a storage location remote from the ultrasound imaging system in a diagnostic medical imaging network.

22. The method of claim 15, wherein (a) comprises archiving a user-adjusted ultrasound parameter characteristic of a first ultrasound image with an ultrasound imaging system different from the ultrasound imaging system that automatically implements in (c).

23. The method of claim 15, further comprising the step of:
(d) with the ultrasound imaging stem, acquiring a second ultrasound image using said user-adjusted ultrasound parameter implemented in step (c).

24. The invention of claim 15, wherein said first ultrasound image is associated with a first patient and wherein said second ultrasound image is associated with a second patient.

25. A method for automatically displaying a retrieved ultrasound parameter, said method comprising the steps of;
(a) archiving an ultrasound parameter comprising at least one parameter selected from the group consisting of a user-controlled B-mode field of view parameter, a user-controlled region displaying color-Doppler information parameter, and a user-controlled depth-dependent gain compensation parameter; then
(b) with an ultrasound imaging system retrieving said ultrasound parameter; and then
(c) with the ultrasound imaging system, automatically displaying said retrieved ultrasound parameter.

26. The method of claim 25, further comprising the step of:
(d) with the ultrasound imaging system, automatically implementing said retrieved ultrasound parameter.

27. The method of claim 25, further comprising the step of archiving an ultrasound image with said ultrasound parameter.

28. The method of claim 27, further comprising the step of retrieving said ultrasound image with said ultrasound parameter.

29. The method of claim 25, wherein step (a) comprises the step of archiving an ultrasound parameter comprising at least one parameter selected from the group consisting of a user-controlled B-mode field of view parameter, a user-controlled region displaying color-Doppler information parameter, and a user-controlled depth-dependent gain compensation parameter in a storage location in the ultrasound imaging system.

30. The method of claim 25, wherein step (a) comprises the step of archiving an ultrasound parameter comprising at least one parameter selected from the group consisting of a user-controlled B-mode field of view parameter, a user-controlled region displaying color-Doppler information parameter, and a user-controlled depth-dependent gain compensation parameter in a storage location remote from the ultrasound imaging system in a diagnostic medical imaging network.

31. The method of claim 25, wherein (a) comprises archiving an ultrasound parameter with an ultrasound imaging system different from the ultrasound imaging system that automatically displays in (c).

32. A method for automatically comparing and implementing ultrasound parameters, said method comprising the steps of
(a) with an ultrasound imaging system, retrieving a first ultrasound system identification parameter characteristic of a first ultrasound image;
(b) with the ultrasound imaging system, automatically comparing said retrieved first ultrasound system identification parameter to a second ultrasound system identification parameter;
(c) with the ultrasound imaging system, automatically notifying an operator of a discrepancy between said retrieved first ultrasound system identification parameter and said second ultrasound system identification parameter;
(d) with the ultrasound imagine system, retrieving a first ultrasound user-adjusted parameter characteristic of said first ultrasound image; and
(e) with the ultrasound imaging system automatically implementing said retrieved first ultrasound user-adjusted parameter before acquiring a second ultrasound image.

33. The invention of claim 32, wherein said first ultrasound image is associated with a first patient and wherein said second ultrasound image is associated with a second patient.

34. An ultrasound imaging system comprising:
an ultrasound image acquisition, processing, and display system;
a storage device coupled with said ultrasound image acquisition, processing, and display system;
means, coupled with said storage device, for archiving in said storage device a first ultrasound parameter characteristic of a first ultrasound image;
means, coupled with said storage device, for retrieving said first ultrasound parameter from said storage device; and
means for automatically comparing said retrieved first ultrasound parameter to a second ultrasound parameter.

35. The invention of claim 34, further comprising:
means for automatically notifying an operator of a discrepancy between said retrieved first ultrasound parameter and said second ultrasound parameter.

36. The invention of claim 34, further comprising:
means for automatically implementing said retrieved first ultrasound parameter in said ultrasound image acquisition, processing, and display system.

37. An ultrasound imaging system comprising:
an ultrasound image acquisition, processing, and display system;
a storage device coupled with said ultrasound image acquisition, processing, and display system;
means, coupled with said storage device, for archiving in said storage device a user-adjusted ultrasound parameter characteristic of a first ultrasound image;
means, coupled with said storage device, for retrieving said user-adjusted ultrasound parameter from said storage device; and means for automatically implementing said retrieved user-adjusted ultrasound parameter in said ultrasound image acquisition, processing, and display system before acquiring a second ultrasound image.

38. An ultrasound imaging system comprising:

an ultrasound image acquisition, processing, and display system;

a storage device coupled with said ultrasound image acquisition, processing, and display system;

means, coupled with said storage device, for archiving in said storage device an ultrasound parameter comprising at least one parameter selected from the group consisting of a user-controlled B-mode field of view parameter, a user-controlled region displaying color-Doppler information parameter, and a user-controlled depth-dependent gain compensation parameter;

means, coupled with said storage device, for retrieving said ultrasound parameter from said storage device; and means for automatically displaying said retrieved ultrasound parameter.

39. An ultrasound imaging system comprising:

an ultrasound image acquisition, processing, and display system;

a storage device coupled with said ultrasound image acquisition, processing, and display system;

means, coupled with said storage device, for retrieving a first ultrasound system identification parameter characteristic of a first ultrasound image from said storage device;

means, coupled with said storage device, for automatically comparing said retrieved first ultrasound system identification parameter to a second ultrasound system identification parameter;

means for automatically notifying an operator of a discrepancy between said retrieved first ultrasound system identification parameter and said second ultrasound system identification parameter;

means, coupled with said storage device, for retrieving a first ultrasound user-adjusted parameter characteristic of said first ultrasound image; and means for automatically implementing said retrieved first ultrasound user-adjusted parameter in said ultrasound image acquisition, processing, and display system before acquiring a second ultrasound image.

40. A medical diagnostic imaging network comprising:

a first ultrasound imaging system;

a storage device remotely located from and coupled with said first ultrasound imaging system;

first means, coupled with said storage device, for archiving in said storage device a first ultrasound parameter characteristic of a first ultrasound image of said first ultrasound imaging system;

second means, coupled with said storage device, for retrieving said first ultrasound parameter from said storage device; and third means for automatically comparing said retrieved first ultrasound parameter to a second ultrasound parameter of an ultrasound imaging system coupled with said storage device.

41. The invention of claim 40, further comprising a second ultrasound imaging system coupled with said storage device.

42. The invention of claim 40, further comprising fourth means for automatically notifying an operator of a discrepancy between said retrieved first ultrasound parameter and said second ultrasound parameter.

43. A medical diagnostic imaging network comprising:

a first ultrasound imaging system;

a storage device remotely located from and coupled with said first ultrasound imaging system;

first means, coupled with said storage device, for archiving in said storage device a user-adjusted ultrasound parameter characteristic of a first ultrasound image of said first ultrasound imaging system;

second means, coupled with said storage device, for retrieving said user-adjusted ultrasound parameter from said storage device; and third means for automatically implementing said retrieved user-adjusted ultrasound parameter in an ultrasound imaging system coupled with said storage device.

44. The invention of claim 43, further comprising a second ultrasound imaging system coupled with said storage device.

45. A medical diagnostic imaging network comprising:

a first ultrasound imaging system;

a storage device remotely located from and coupled with said first ultrasound imaging system;

first means, coupled with said storage device, for archiving in said storage device an ultrasound parameter comprising at least one parameter selected from the group consisting of a user-controlled B-mode field of view parameter, a user-controlled region displaying color-Doppler information parameter, and a user-controlled depth-dependent gain compensation parameter of said first ultrasound imaging system;

second means, coupled with said storage device, for retrieving said ultrasound parameter from said storage device; and third means for automatically displaying said retrieved ultrasound parameter in an ultrasound imaging system coupled with said storage device.

46. The invention of claim 45, further comprising a second ultrasound imaging system coupled with said storage device.

* * * * *

UNITED STATES PATENT AND TRADEMARK OFFICE
CERTIFICATE OF CORRECTION

PATENT NO.   : 5,997,478
DATED        : December 7, 1999
INVENTOR(S)  : John I. Jackson et al.

It is certified that error appears in the above-identified patent and that said Letters Patent is hereby corrected as shown below:

Claims
Claim 1,
Line 5, please insert -- , -- immediately after "system".
Line 6, please change "," (comma) to -- ; -- (semicolon).

Claim 11,
Line 4, please change "imagine" to -- imaging --.

Claim 23,
Line 3, please change "stem" to -- system --.

Claim 25,
Line 2, please change ";" (semicolon) to -- : -- (colon).
Line 9, please insert -- , -- immediately after "system".

Claim 32,
Line 3, please insert -- : -- (colon) immediately after "of".
Line 19, please insert -- , -- (comma) immediately after "system".

Signed and Sealed this

Eleventh Day of September, 2001

*Attest:*

*Attesting Officer*

NICHOLAS P. GODICI
*Acting Director of the United States Patent and Trademark Office*